(12) United States Patent
Proksa

(10) Patent No.: US 6,817,762 B2
(45) Date of Patent: Nov. 16, 2004

(54) FLUOROSCOPY INTERVENTION METHOD WITH A CONE-BEAM

(75) Inventor: Roland Proksa, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/297,855

(22) PCT Filed: Apr. 9, 2002

(86) PCT No.: PCT/IB02/01116
§ 371 (c)(1),
(2), (4) Date: Dec. 10, 2002

(87) PCT Pub. No.: WO02/058212
PCT Pub. Date: Oct. 31, 2002

(65) Prior Publication Data
US 2003/0147492 A1 Aug. 7, 2003

(30) Foreign Application Priority Data
Apr. 10, 2001 (EP) .............................. 01201324

(51) Int. Cl.[7] .................................. A61B 6/08
(52) U.S. Cl. .................. 378/206; 600/425; 600/427
(58) Field of Search ............... 378/19, 4, 98, 378/98.8, 206, 205, 63; 600/425, 427, 426

(56) References Cited

U.S. PATENT DOCUMENTS

| 4,485,815 A | | 12/1984 | Amplatz | |
|---|---|---|---|---|
| 5,873,826 A | * | 2/1999 | Gono et al. | 600/425 |
| 6,122,541 A | * | 9/2000 | Cosman et al. | 600/426 |
| 6,167,296 A | * | 12/2000 | Shahidi | 600/427 |
| 6,435,717 B1 | * | 8/2002 | Kohler et al. | 378/206 |
| 6,477,400 B1 | * | 11/2002 | Barrick | 600/426 |
| 6,481,888 B1 | * | 11/2002 | Morgan | 378/204 |
| 6,484,049 B1 | * | 11/2002 | Seeley et al. | 600/426 |
| 6,542,770 B2 | * | 4/2003 | Zylka et al. | 600/424 |

* cited by examiner

Primary Examiner—David V. Bruce
Assistant Examiner—Irakli Kiknadze
(74) Attorney, Agent, or Firm—Thomas M. Lundin

(57) ABSTRACT

A fluoroscopy intervention method to obtain an image of an object (11) together with radiopaque intervention means (30), the method using a rotating cone-beam X-ray source (8,9) and a corresponding two-dimensional X-ray detector (6) with the object (11) and the intervention means (30) positioned between the X-ray source (8) and the X-ray detector (6). Due to a cone-beam acquisition and a multislice reconstruction (9') the intervention means (30) can have a substantial angulation with respect to the image slices (9'), providing the operator's hand (4) being outside the primary X-ray beam (9). This reduces the X-ray dose the operator. By providing additional lighting means (60), delineating the primary X-ray source at its periphery, the operator is supplied with an information about the spatial position of the X-ray radiation. The lighting means (60) can be further used to position an X-ray shield (65) of a surface of the patient to reduce the X-ray dose due to scattered radiation.

6 Claims, 2 Drawing Sheets

FLUOROSCOPY INTERVENTION METHOD WITH A CONE-BEAM

BACKGROUND

Figure 1A:
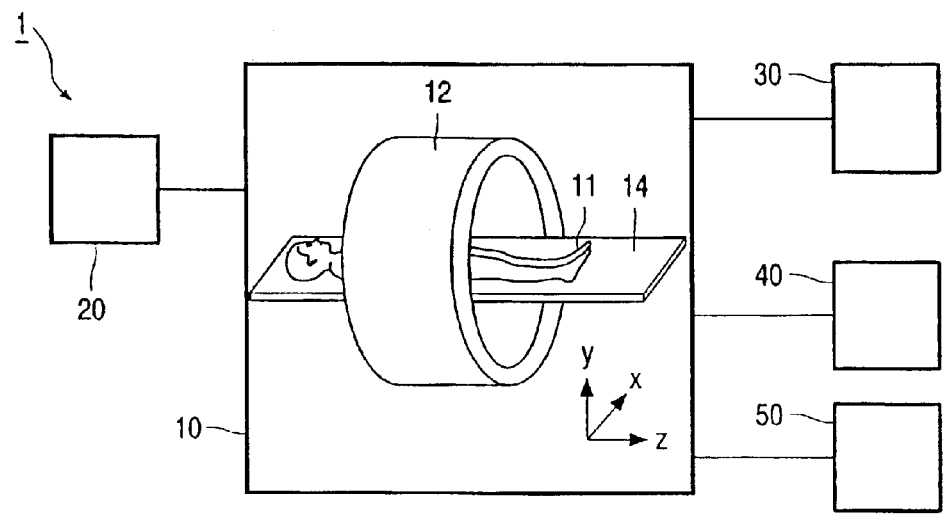

The present invention relates to a fluoroscopy method for obtaining an image of an object together with radiopaque intervention means, the method using a rotating X-ray source and a corresponding detector with the object and the intervention means positioned between the X-ray source and the detector, the method further using processing means, said method comprising subjecting the object to the X-rays originating from the X-ray source; positioning the intervention means within the object, such that they intercept at least a part of said X-rays; using the processing means to present a spatial position of the intervention means with respect to the object.

The present invention relates also to a system for carrying out the fluoroscopy method according to the invention.

According to a general practice of conventional fluoroscopic intervention, the intervention means are guided within the patient by means of, for example a CT-apparatus. In this case the operator inserts, for example, a needle into the patient, while the intervention means are located within the primary X-ray beam, exposing an interesting volume of the patient, so that it can be localized on a transmission image of the patient. The width of the primary beam is comparable with a cross-section of the intervention means, because the dimensions of the beam correlate with a slice thickness of the CT image. It is important to have the tip of the intervention means together with the surrounding anatomy of the patient within the image. Therefore, the beam width must not be too small and the angle between the needle and the image plane must be small. Given these constrains the operator hand can hardly be protected from a direct X-ray exposure.

The problem of the X-ray dose to the operator's hand is addressed in U.S. Pat. No. 4,485,815. This document discloses a fluoroscopy method for performing percutaneous puncture treatment, wherein the intervention means are supplied with an adjustment comprising an elongated radiolucent handle, so that the operator's hands are substantially removed from the area of primary X-ray beam. The intervention means are positioned substantially parallel to the primary X-ray beam. The movement of the intervention means is continuously monitored on a fluoroscope monitor, the intervention means being viewed in cross-section. The problem of the known method lies in the construction of the provided handle, increasing the working lever experienced by the operator to maneuver the intervention means. The accuracy of the such a positioning of the intervention means is a critical issue, especially when working within a critical area, such as a brain. Another problem of the known fluoroscopic method is the fact that the needle is presented only as a transversal cross-section, providing a limited information about the position of the needle tip within the patient.

SUMMARY

It is an object of the invention to provide a fluoroscopic method, wherein the dose to the operator is decreased, whereas the intervention means can be easily positioned within the patient. The fluoroscopic method according to the invention is characterized by a cone beam being used as the X-ray source, a two-dimensional detector being used as the detector. According to this technical measure, the generated X-ray beam will propagate substantially in three dimensions, illuminating a two-dimensional X-ray detector, thus providing three-dimensional volume data of the patient and the intervention means, based on the acquisition of two-dimensional projections from, for example, one rotation. Due to a cone-beam acquisition the intervention means can have a substantial angulation with respect to the image slices, providing the operator's hand being outside the primary X-ray fluence. This reduces the X-ray dose to the operator's hand substantially.

A preferred embodiment of the fluoroscopic method according to the invention is characterized in that the spatial position of the intervention means within the object is presented within one image reconstruction slice by means of an image reconstruction algorithm. Since the operator can hardly inspect a set of two-dimensional slices during the intervention, a single reconstructed image provides all important information about the spatial position of the intervention means with respect to the local anatomy of the patient. The extended image volume covered by a set of two-dimensional slices can be used to obtain the important image information around the tip of the intervention means, for example a needle. Since the individual slices in the cone beam geometry are thinner than the complete illuminated volume limited by the cone beam geometry, the inherent resolution of the image information can be high and is mainly defined by the resolution of the X-ray detector in a longitudinal direction. An example of a suitable image reconstruction algorithm is a known method of volume rendering or a known method of multi-planar reformatting, both being an interpolation technique to generate a virtual image oblique to the set of image planes. An example and application of such image reconstruction algorithms is given in an "Easy Vision" Product Manual, Philips Medical Systems. The oblique image should be positioned within the imaged volume such that, for example, the biopsy needle is located within the virtual slice. This particular embodiment ensures reduced radiation to the operator and a high resolution of the resulting reconstructed image that covers the tip of the needle and the surrounding anatomy of the patient.

Another embodiment of the fluoroscopy method according to the invention is characterized in that the position and the orientation of said reconstruction slice is a-priori calculated. In case the optimal trajectory of the needle path is pre-planned based on a static image acquisition, it is possible to use the coordinates of the pre-planned path to orient the image reconstruction plane. In this case the image reconstruction plane is fixed during the procedure and the operator is maneuvering the intervention means so that they stay in the pre-determined plane during the procedure. An application of this technique is known from Proksa et al 'Navigation Support for CT-guided interventional radiology', ECR99, Vienna 1999.

Another embodiment of the fluoroscopy method according to the invention is characterized in that the position and the orientation of said reconstruction slice is determined with respect to the on-line reconstructed image of the intervention means. Since the biopsy needle is made of a radiopaque material, it will be imaged with a high contrast with respect to the surrounding patient anatomy. Therefore, it is possible to perform an on-line detection of pixel values, above a certain threshold for the X-ray absorption, in order to reconstruct the needle in three-dimensions. For this purpose one can use a variety of known image registration techniques. A plane cutting the line corresponding with the coordinates of the needle in three-dimensions will be the image reconstruction plane. An advantage of this approach is the possibility to guide the reconstruction plane in a dynamic mode, according to the movement of the needle within the patient anatomy.

Another embodiment of the fluoroscopy method according to the invention is characterized in that the intervention means are provided with position detection means, the processing means comprising further means for determining the position of the intervention means relative to the object. The biopsy needle could be combined with means to register the position and orientation of the needle relative to the CT-scanner. The measurement could be similar to the technique presented by Proksa et al 'Navigation Support for CT-guided interventional radiology', ECR99, Vienna 199. During the examination the physician introduces a surgical or interventional instrument, such as a biopsy needle, into the body of the patient. The surgical instrument is provided with transmission elements such as diodes emitting light or infrared radiation (LEDs or IREDs). Such a computed tomography device includes a position measuring system with a camera unit mounted, for example on a mast. The position measuring system comprises the camera unit and a computer. The computer is connected to the camera unit so that the camera unit can supply the computer with image signals. The camera unit picks up images of the transmission elements on the surgical instrument from different directions and a computer computes the position of the surgical instrument relative to the camera unit from said images. Furthermore, transmission elements, for example LEDs or IREDs again, are also provided on the gantry of the computed tomography device. The camera unit also picks up images of the transmission elements on the gantry and the computer computes the position of the gantry relative to the camera unit from these images. The position of the gantry is related directly to the position of the cross-section of the patient of which a slice image is formed in the relevant position of the gantry. It has been found that the relationship between the gantry positions measured by the camera unit and the position of the cross-section of the patient which is imaged in the slice image be accurately calibrated. The transformation of positions in said cross-section to corresponding positions in the slice image can be derived from the calibrated relationship between the position of the gantry and the position of the cross-section of the patient imaged in this position of the gantry. On the basis of the positions, measured by the camera unit, of on the one hand the surgical instrument and on the other hand the position of the gantry, also measured by the camera unit, and the position, derived therefrom, of the cross-section of the patient which is reproduced in the slice image, it is possible to reproduce, using the transformation, also the corresponding position of the surgical instrument in the rendition of the slice image. The physician, for example a surgeon or radiological interventionist, can thus track the surgical instrument within the body of the patient in the image without having a direct view of the instrument. A CT-apparatus of this kind is described in European patent application No. 98202074.5.

The present invention relates also to a system for carrying out the fluoroscopy method according to the invention. The system according to the invention comprises a CT-apparatus, including an X-ray source for producing a cone beam, driving means to move the X-ray source in an arc in a plane, a two dimensional X-ray detector, intervention means, first processing means for carrying out image reconstruction algorithms, second processing means for determining an image reconstruction slice. According to the system of the invention the X-ray beam is produced by a CT-apparatus, the X-ray beam being the cone beam. By combining the cone-beam geometry with a corresponding two-dimensional X-ray detector, the volume data is acquired during one run of the X-ray source along an arc about the patient. Using the processing means for the image reconstruction the spatial position of, for example, a needle can be determined with respect to the patient anatomy. This position of the used by the second processing means to calculate the image reconstruction plane for further needle positioning within the patient.

Another embodiment of the system according to the invention is characterized in that the system further comprises lighting means to generate a light beam propagating substantially in a plane parallel to a plane adjacent to an edge of the cone-beam, spatially delineating the cone-beam it its exterior. Since the cone-beam rotates, the angle of a lighted plane would also rotate. Therefore, it is preferable to arrange the lighting means so that the lighted plane is perpendicular to the radiation axis of the cone-beam. This means that for a given tube position the lighted plane can only be close to the periphery of the X-ray beam. By using this technical measure the operator is provided with a spatial delineation of the periphery of the X-ray beam. Thus, the operator can position the intervention instrument with such an angulation with respect to the periphery of the cone beam that his hand does not intercept the beam of the primary X-rays. This measure assures the minimization of the dose to the operator's hand during a fluoroscopic intervention procedure. A method to visualize a primary X-ray beam is known per se from U.S. Pat. No, 5,873,826. In this document, a sing is shown provided with lighting means to visualize the solid angle thorough which no primary X-rays are passing during a revolution of the X-ray source. The known CT-apparatus is further supplied with dose control means for changing an X-ray radiation dose within an angular range during a rotation of the X-ray tube. As explained earlier due to single-slice acquisition with a small slice thickness the operator's hand is unavoidably positioned within the solid angle of the primary X-rays. The known CT-apparatus presents possibility to reduce the dose to the operator's hand by setting the dose of the primary radiation to zero or to a low value in the range of angles, corresponding to the operator's hand position.

According to the system of the invention no X-ray modulation is necessary, firstly because due to the cone-beam acquisition a substantial angulation between a needle and the slice planes is allowed, and secondly because the lighting means are positioned substantially parallel to the periphery of the cone-beam, propagating in a plane parallel to the source rotation, delineating the space where the X-rays are propagating.

A further embodiment of the system according to the invention is characterized in that the system further comprises X-ray shielding means to be positioned substantially in the vicinity of the edge of the cone beam at its exterior. It is generally understood that the operator's hand receives the dose of the X-ray radiation due to the sum of the primary and scattered radiation. According to a common practice the shielding means are positioned somewhere near the primary beam. In case the acquisition is performed with a single-slice CT-apparatus, the shielding means are not effective for reducing the dose to the operator's hand, as the majority of the acquired dose by the operator corresponds to the primary X-ray beam. The origin of the majority of scattered radiation is within the patient. By placing an X-ray radiation shield on the surface of the patient, the dose to the operator's hand can be further reduced. By using the lighting means, arranged in the vicinity of the edge of the cone beam at its exterior, the shielding means could be positioned as close as possible to the cone beam, yet not intercepting it.

These and other aspects of the invention will be further explained with reference to the figures, where the corresponding numerals depict the corresponding elements.

DRAWINGS

FIG. 1a presents a schematic view of an embodiment of the fluoroscopy system according to the invention.

Figure 1B:
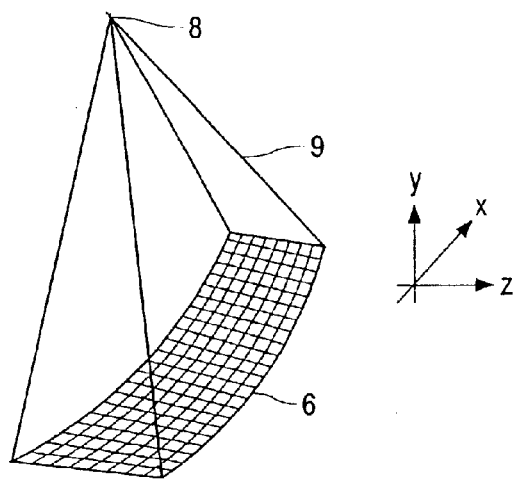

FIG. 1b presents a schematic view of the geometry of the X-ray cone beam and a corresponding two-dimensional X-ray detector.

Figure 1C:
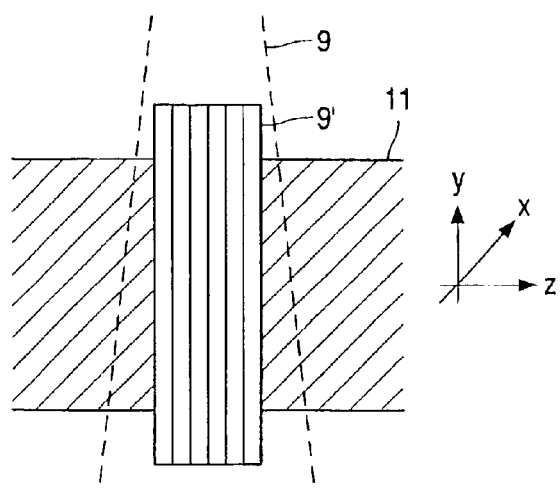

FIG. 1c presents a schematic view of the resulting image reconstruction slices.

Figure 2:
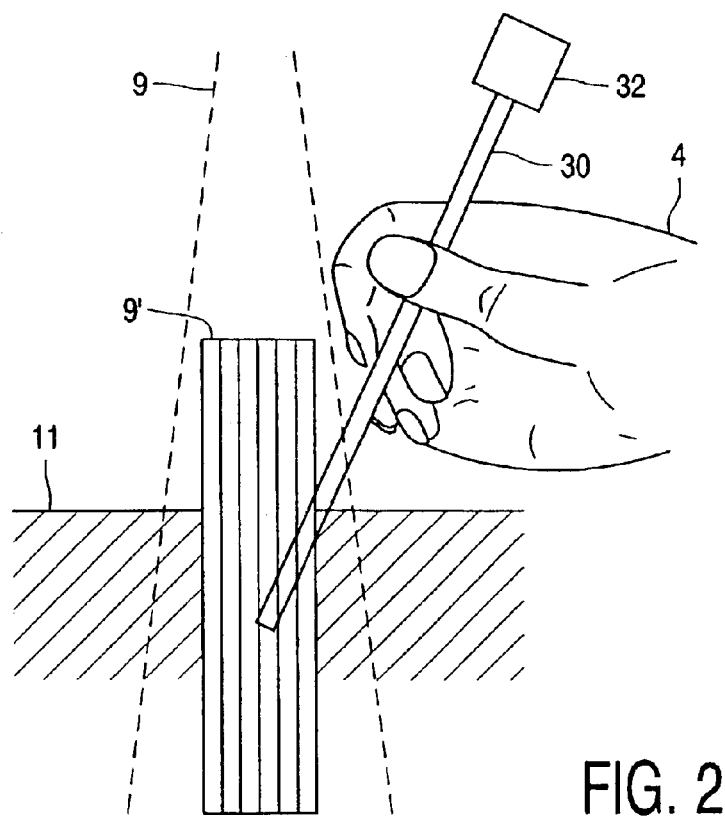

FIG. 2 presents a schematic view of the intervention geometry with respect to the image reconstruction slices.

Figure 3:
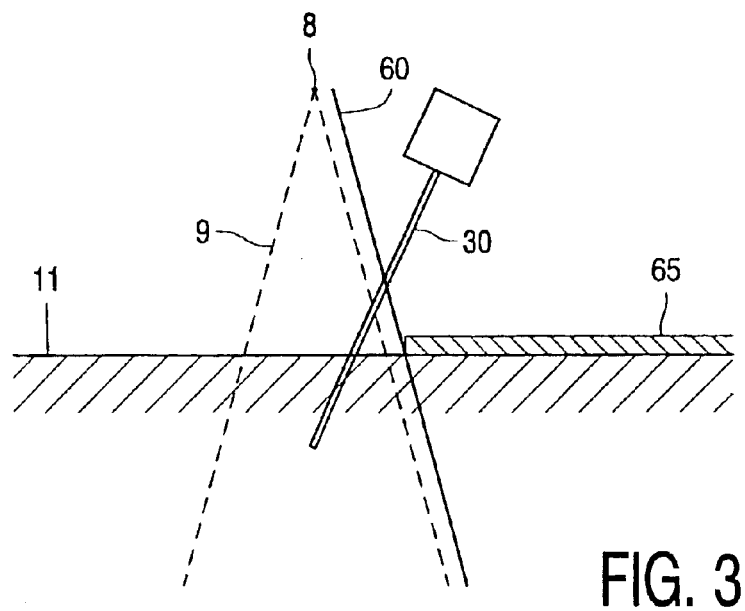

FIG. 3 presents a schematic view of the lighting means to be arranged at the periphery of the cone-beam.

DESCRIPTION

FIG. 1a presents in a schematic way an embodiment of the system 1 according to the invention. The system comprises a CT-apparatus 10, wherein a patient 11 to be examined is positioned on a patient support table 14 and is located within a volume of a CT-gantry 12. The patient 11 is irradiated with a cone-beam of X-rays propagating from an X-ray source (not shown in the figure), arranged within the CT-gantry 12. The CT-apparatus comprises further driving means 20 to rotate the X-ray source around the patient 11. The transmission image is acquired by a two-dimensional X-ray detector (not shown in the figure), arranged within the CT-gantry 12. The fluoroscopy system 1 further comprises intervention means 30 to be positioned within the patient 11, according to a fluoroscopy intervention procedure. The fluoroscopy system according to the invention further comprises first processing means 40 to perform a reconstruction of the cone-beam slices based on the acquired data as well as second processing means 50 to determine the image reconstruction slice, presenting the intervention means 30 together with a surrounding patient anatomy.

FIG. 1b presents a schematic view of the geometry of the X-ray cone-beam and a corresponding two-dimensional X-ray detector. The X-ray source 8, arranged within the gantry of the CT-apparatus 10, shown in FIG. 1, generates the X-rays, which are propagating within a cone 9. A patient to be examined together with the intervention means 30, shown in FIG.1 are positioned in the CT-gantry 12 between the X-ray source 8 and the X-ray detector 6, the transmitted X-rays being intercepted by the X-ray detector 6. The X-ray source 8 is rotated around the axis z in a plane within the gantry of the CT-apparatus to provide a set of two-dimensional transmission data, representing the irradiated tree-dimensional patient volume.

FIG. 1c presents a schematic view of the resulting image reconstruction slices obtained using the first processing means 40. The image reconstruction is preformed by means of the first processing means 40 in a manner well known in the art, resulting in a number of two-dimensional slices 9', presenting the anatomy of the patient 11 together with an information on the intervention means 30, not shown in the figure. The reconstruction slices 9' are obtained based on the acquisition of the two-dimensional projections on the X-ray detector, resulting in number of two-dimensional slices at different z positions. Since the individual slices 9' are thinner than the complete irradiated volume limited by the cone-beam geometry, the inherent resolution of the image reconstruction can be high and is mainly determined by the resolution of the X-ray detector in z-direction.

FIG. 2 presents a schematic view of the intervention geometry with respect to the image reconstruction slices 9'. Due to the fact that the image reconstruction is performed in a multi-slice mode, the intervention tool, for example a biopsy needle 30 does not have to be delineated by a single slice and, therefore, it can have a substantial angulation with respect to the set of the slices. In this case the operator's hand 4 is positioned outside the primary X-ray beam 9, minimizing the X-ray exposure to the operator. The extended image volume covered by the set of two-dimensional slices 9' can be used to obtain important image information around the tip of the needle 30. By reconstructing the spatial position of the needle an oblique reconstruction slice is defined. This procedure is well known in the art. By presenting this oblique reconstruction by means of not shown second processing means it is possible to present the information about the spatial position of the needle with respect to the adjacent patient anatomy, which simplifies an inspection procedure to be performed operator. It is also possible to provide the needle with position detection means 32 to register the position of the needle relative to the CT-scanner and to the patient. A method of this kind is described in European patent application No. 98202074.5. According to this met also possible to provide information about the spatial orientation of the oblique slice to be reconstructed for guiding purposes.

FIG. 3 presents a schematic view of the lighting means 60 to be arranged at the periphery of the cone-beam. The lighting means 60 emit a visible light in order to spatially delineate the periphery of the primary X-ray beam 9 at its exterior. To obtain this a source of the visible light, for example a light-emitting diode, is arranged in the vicinity of the periphery of the X-ray beam in a plane, close to a plane corresponding to the periphery of the cone-beam, adjacent to an edge of the cone-beam, spatially delineating the cone-beam it its exterior. Due to this technical measure, the operator is informed about the spatial position of the X-rays and he can take this into account while positioning the needle 20 within the patient 11. It is also possible to introduce a number of lighting means arranged parallel to each other and with a different distance to the periphery of the X-ray source, for example a number of diodes emitting, for example, different monochromatic light, each color corresponding with a certain isodose around the primary X-ray beam, for example with 10%, 50% and 95%, respectively. It is also possible to use the lighting means to inform the operator about the distance of his hand to the X-ray beam. This is useful because the operator should avoid, for example, the inner light being intercepted by his hand.

It is generally understood that the total dose, received by the operator's hand is a sum of the primary and scattered radiation. By using the lighting means 60 it is possible to position X-ray shielding means 65, for example a lead plate in the direct vicinity of the primary X-ray beam 9, yet not intercepting it. The shielding means 65 serves to intercept the scattered radiation, originating within the irradiated volume of the patient. Due to this technical measure the X-ray dose to the operator's hand can be further reduced.

What is claimed is:

1. A fluoroscopy method for obtaining an image of an object (11) together with radiopaque intervention means (30), the method using a rotating X-ray source (8) and a corresponding detector (6) with the object and the intervention means positioned between the X-ray source and the detector, the method further using processing means, said method comprising subjecting the object to the X-rays (9) originating from the X-ray source:

positioning the intervention means (30) within the object (11), such that they intercept at least a part of said X-rays (9);

using the processing means (40) to present a spatial position of the intervention means (30) with respect to the object; characterized by a cone beam (9) being used as the X-ray source, a two-dimensional detector (6) being used as the detector and further comprising:

generating a light beam propagating substantially in a plane adjacent to an edge of the cone-beam, spatially delineating the cone-beam it its exterior.

2. A fluoroscopy method according to claim 1, wherein the spatial position of the intervention means (30) within the object (11) is presented within one image reconstruction slice by means of an image reconstruction algorithm.

3. A fluoroscopy method according to claim 2, wherein the position and the orientation of said reconstruction slice is a-priori calculated.

4. A fluoroscopy method according to claim 2, wherein the position and the orientation of said reconstruction slice is determined with respect to the on-line reconstructed image of the intervention means (30).

5. A fluoroscopy method according to claim 4, wherein the intervention means (30) are reconstructed using a three-dimensional image registration technique.

6. A fluoroscopy method according to claim 4, wherein the intervention means (30) are provided with position detection means (32), the processing means comprising further means for determining the position of the intervention means relative to the object (11).

* * * * *